(12) United States Patent
Pearl

(10) Patent No.: US 7,427,753 B2
(45) Date of Patent: Sep. 23, 2008

(54) METHOD OF CROSS-SECTION MILLING WITH FOCUSED ION BEAM (FIB) DEVICE

(75) Inventor: Asher Pearl, Kadimah (IL)

(73) Assignee: Applied Materials, Israel, Ltd., Rehovot (IL)

( * ) Notice: Subject to any disclaimer, the term of this patent is extended or adjusted under 35 U.S.C. 154(b) by 443 days.

(21) Appl. No.: 11/153,953

(22) Filed: Jun. 16, 2005

(65) Prior Publication Data

US 2006/0286772 A1 Dec. 21, 2006

(51) Int. Cl.
*G01N 31/00* (2006.01)
*G01N 33/00* (2006.01)

(52) U.S. Cl. .................. 250/304; 250/310; 250/306; 250/307; 250/309; 250/492.1; 250/492.21; 250/492.3; 438/460; 438/24; 438/14; 438/16

(58) Field of Classification Search .................. 250/310, 250/304, 306, 307, 309, 492.1, 492.21, 492.23; 438/460, 24, 14, 16

See application file for complete search history.

(56) References Cited

U.S. PATENT DOCUMENTS

| 5,093,572 | A | 3/1992 | Hosona |
| 6,211,527 | B1 | 4/2001 | Chandler |
| 6,641,705 | B2 | 11/2003 | Phaneuf |
| 6,670,610 | B2 | 12/2003 | Shemesh |
| 6,768,110 | B2 | 7/2004 | Alani |

*Primary Examiner*—Jack Berman
*Assistant Examiner*—Meenakshi S Sahu
(74) *Attorney, Agent, or Firm*—Reinhold Cohn and Partners

(57) ABSTRACT

A method of milling a cross section of a wafer and a milling device. The method includes a coarse scanning of at least two milling frames and a fine scanning of at least one milling frame. The milling device is adapted to cross-section milling of a wafer, said milling includes a coarse scanning of at least two milling frames and a fine scanning of at least one milling frame.

20 Claims, 10 Drawing Sheets

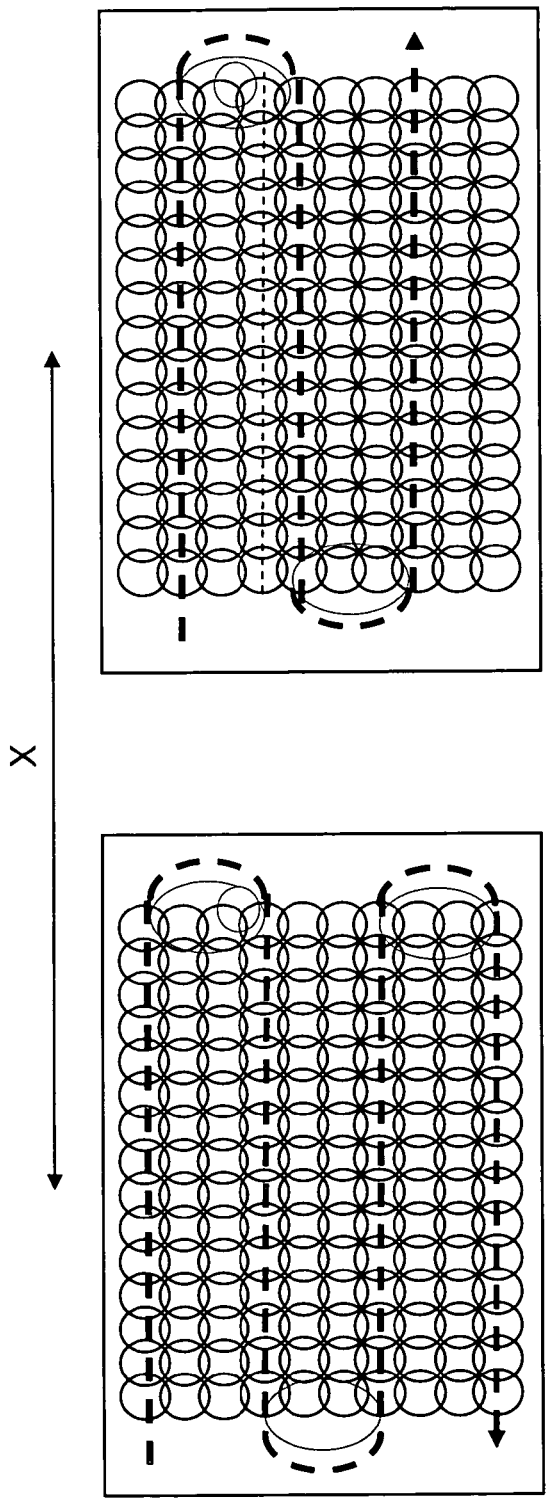
Figure 8a
Figure 8b
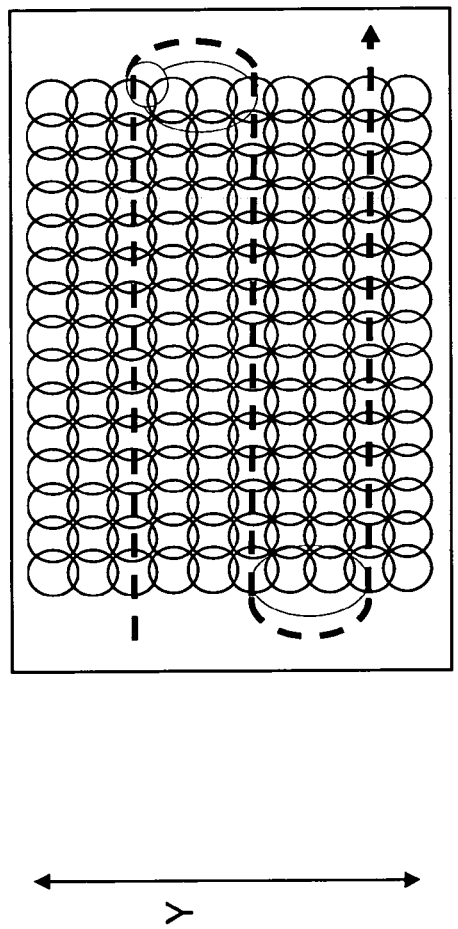
Figure 8c

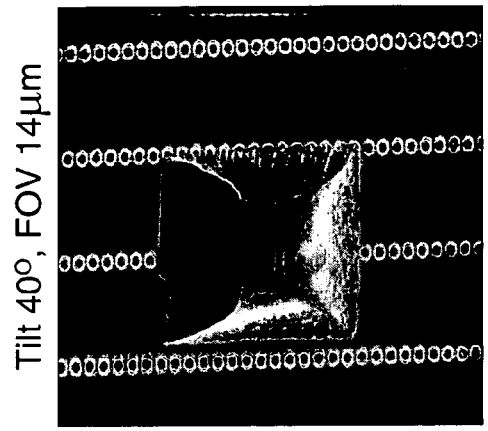
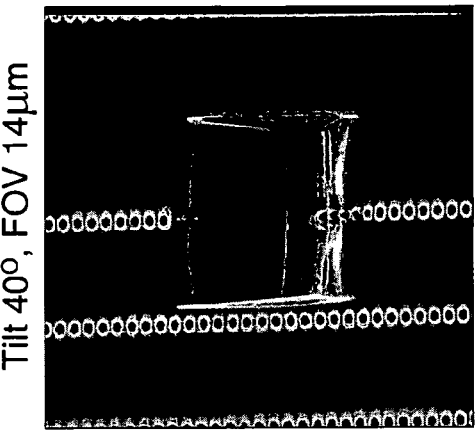
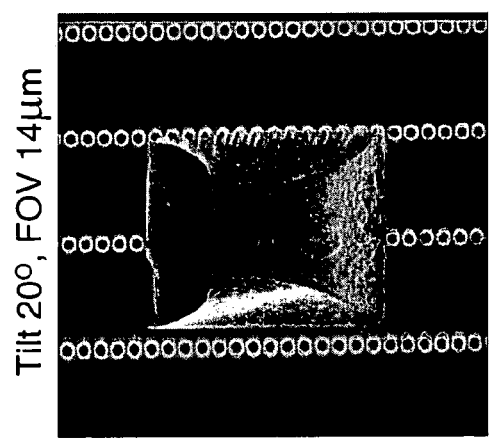
Figure 10a
Figure 10b
Regular milling Cross Section Slope
| Area | 6*8*2μm |
|---|---|
| Probe current | 500 pA |
| Time | 6:30 min |
| Depth | 3.9 μm |
Multi-frame milling Cross Section Slope
| Area | 6*8*0.5μm X4 |
|---|---|
| Probe current | 500 pA |
| Time | 1:37 min |
| Depth | 4.8 μm |

METHOD OF CROSS-SECTION MILLING WITH FOCUSED ION BEAM (FIB) DEVICE

FIELD OF THE INVENTION

This invention relates generally to manufacturing a semiconductor wafer; more specifically, it relates to a method of preparing a cross section in semiconductor wafer, e.g. for further observation and analysis.

BACKGROUND OF THE INVENTION

Focused ion beam (FIB) system is one of the primary tools for examining, analyzing, and repairing processing layers while fabricating of integrated circuits. FIB systems facilitate analyzing defects on in-process wafers as well later diagnosing and correcting the process when a defect does occur. FIB systems are versatile instruments, able to perform a number of operations (including milling, gas assisted etching, deposition, imaging) in various applications as, for example, on-chip circuit modification, mask repair, micro-machining, FIB lithography, end-point detection, advanced circuit diagnostics for failure analysis, micro-manufacturing of objects with micron and submicron sizes, etc.

For example, FIB milling of cross-sections enables to expose underlying layers for observation and testing by removing covering material. The exposed layers may be examined using, for example, the imaging capability of the FIB system, using a scanning electron microscope (SEM) or transmission electron microscope (TEM), etc.

Various implementations of FIB for cross-section milling and further observation are disclosed, for example, in the following patent publications:

U.S. Pat. No. 5,093,572 (Hosono) discloses a scanning electron microscope for cross-section observation capable of cutting more accurately a cross-section of a specific portion of semiconductor wafer in a shorter time, and a cross-section observing method employing such a microscope. The scanning electron microscope includes an SEM column, an FIB column mounted together with SEM column, and a reflected-electron detector for detecting electrons to be reflected from the semiconductor wafer by scanning with an electron beam from the SEM. Thus, since a process of cutting a cross-section to be observed by scanning with an ion beam from FIB column, can be observed in real time by employing the reflected electrons of electron beam from SEM column, a specific portion of the cross section can be cut more accurately in a shorter time.

U.S. Pat. No. 6,211,527 (Chandler) discloses a method for making connections to conductors buried under dielectrics layers using a focused ion beam and an etch-assisting gas, the method allows a via to be milled to contact the conductor without substantial etching and degrading the conductor.

U.S. Pat. No. 6,641,705 (Phaneuf et al.) discloses a method of using a focused ion beam (FIB) apparatus for uniformly removing material, particularly crystalline material, from an area of a target by compensating for or altering the crystal orientation or structure of the material to be removed.

U.S. Pat. No. 6,670,610 (Shemesh et al.) assigned to the assignee of the present application, discloses a system and method for directing a miller. The system includes first images such as a scanning electron microscope, a stage for moving the object and a second imager and miller such as a focused ion beam generator. The object is images to locate a desired location in which the object is to be milled and a landmark that is utilized for directing the miller. The system can include additional steps of milling, analyzing and movement of the object.

U.S. Pat. No. 6,768,110 (Alani) discloses an ion beam milling system and method for electron microscopy specimen preparation, includes vacuum chamber housing ion guns and specimen in holder, with ion beam mask fixed to specimen surface so that no relative movement occurs during milling. The system also includes the ability to view the progress of the milling operation and may include an imaging device such as a light microscope which permits monitoring of the area of interest on a specimen as the specimen is milled.

SUMMARY OF THE INVENTION

In accordance with certain aspects of the present invention, there is provided a method of cross-section milling of a wafer, the method includes coarse scanning comprising at least two milling frames and fine scanning comprising at least one milling frame, while a total milling period of a milling pixel is defined such as to provide a pre-defined milling depth.

In accordance with certain aspects of the present invention, the milling parameters of the coarse scanning differ from the milling parameters of the fine scanning in at least one of the following:
 the beam spot size during the coarse scanning is larger than the beam size during the fine scanning;
 a pixels' overlapping during the coarse scanning is less than during the fine scanning;
 coarse scanning is provided in a line-interlace mode.

In accordance with further aspects of the present invention, the coarse scanning may comprise milling frames each one scanning substantially the same milling lines in the same order and with the substantially the same number of in-frame scanning repetitions of the corresponding line in each frame. Alternatively, the number of scanning lines in milling frames within coarse scanning may grow for each next frame. The total milling period of a milling pixel is defined such as to provide a pre-defined for the coarse scanning milling depth.

In accordance with further aspects of the present invention, the number of scanning repetitions of a corresponding milling line may grow for each next milling frame within the coarse scanning.

In accordance with further aspects of the present invention, at least one milling frame within the fine scanning may comprise at least one line skipped during the coarse scanning. At least one of these skipped lines may be the last line within the milling area.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIG. 8 schematically illustrates line-interlace mode of scanning within a milling frame in accordance with certain embodiments of the present invention FIG. 10 illustrates experimental images of cross-sections received during cross-section milling in accordance with prior art and with certain embodiments of the present invention.

DETAILED DESCRIPTION OF THE INVENTION

There is a need in the art for a novel method and system capable of solving re-deposition problems of the cross-section milling. The invention, in some of its aspects, is aimed at providing a novel method and system capable of facilitating enhanced accuracy of cross-section milling and reducing the overall time of the milling process.

Figure 1:
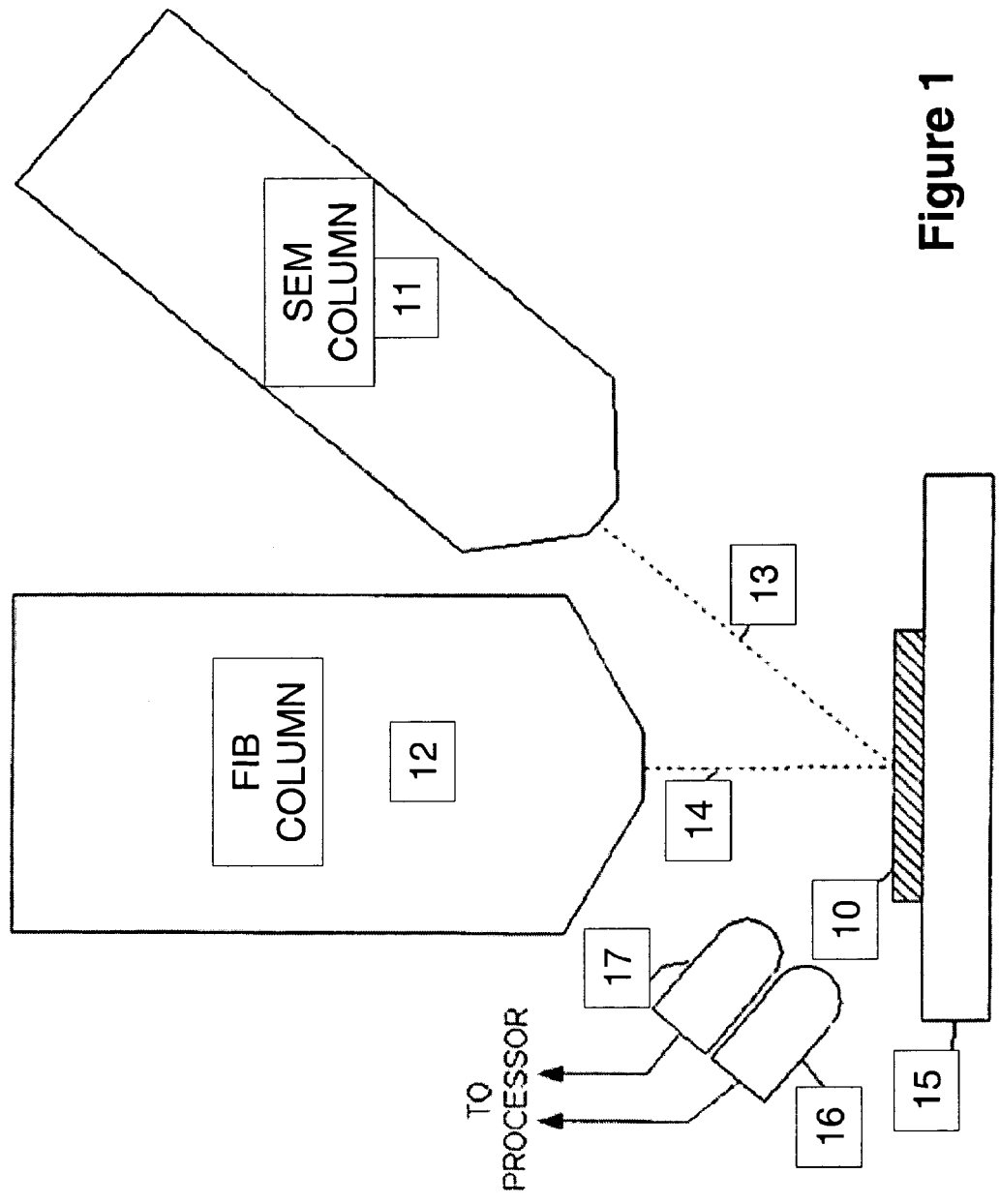
FIGS. 1 and 2 are schematic illustration of exemplary Focused Ion Beam (FIB) systems used in certain embodiments of the present invention.

FIG. 1 illustrates a schematic diagram of an exemplary system for cross-section milling with focused ion beam (FIB). The structure and operation of the FIB are generally known per se and therefore will only be briefly described herein.

In the illustrated example, the system includes a FIB column 12 and a SEM column 11. After the FIB mills the surface and exposes inner layers to inspection, the SEM is utilized to inspect the revealed layers and to further analyze the milled die for detecting defects. The FIB column generates ion beam 14 and the SEM column generates electron beam 13. The FIB/SEM system further has stage 15, detectors 16 and 17 and at least one processor (not shown) coupled to the detectors and being operative to generate images. Stage 15 supports the object, such a wafer 10. Detectors 16 and 17 receive electrons, such as secondary emitted electrons and reflected electrons, emitted or reflected from wafer 10 in response to an irradiation of wafer 10 by electron beam 13 or ion beam 14, and provide detection signals to the processor. The FIB column 12 may be angularly displaced from the SEM column 11 at a predefined angle and be located substantially adjacent to the SEM column as, for example, implemented at XL860 DualBeam Workstation of FEI.

Figure 2:
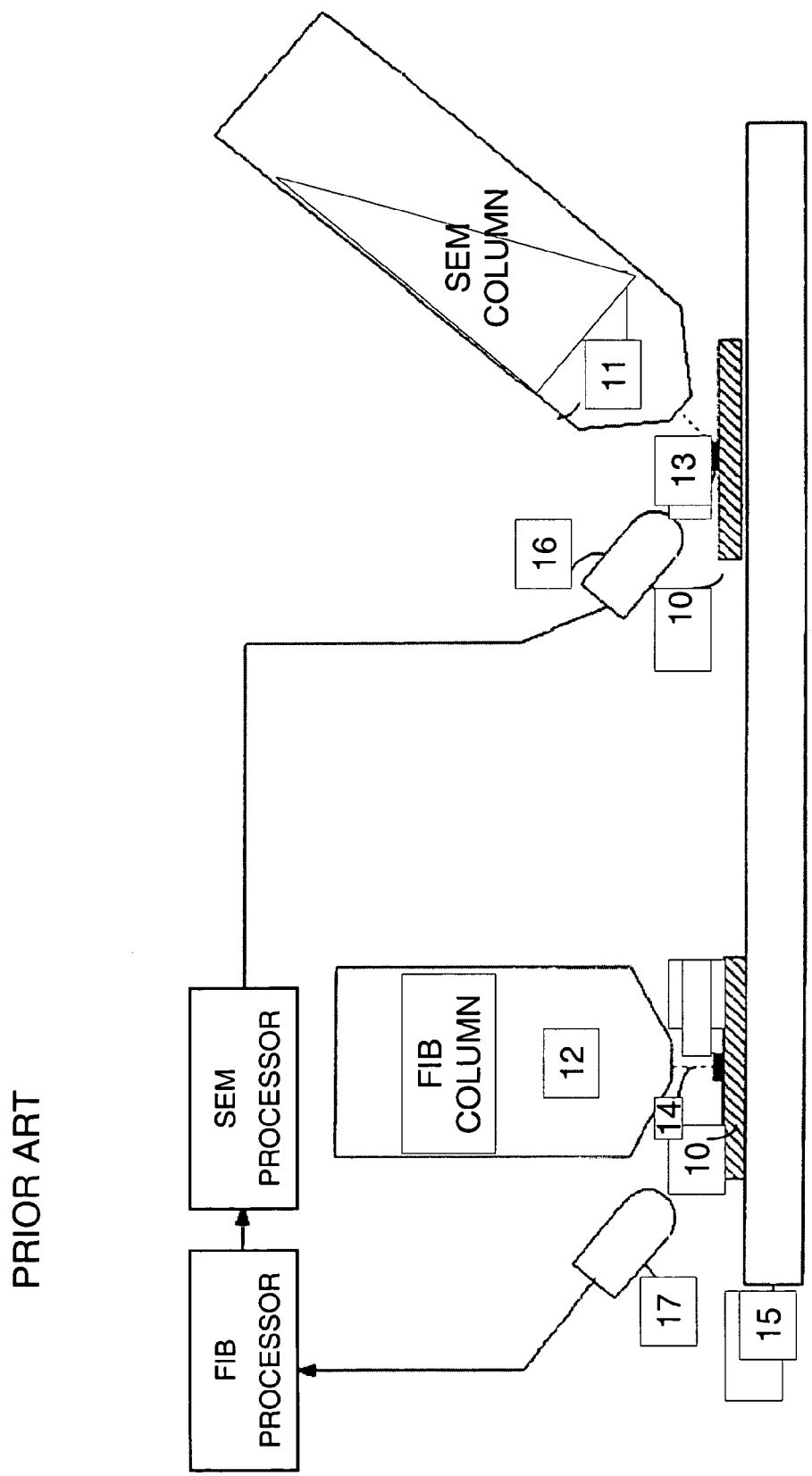

In other example illustrated in FIG. 2, the stage 15 may be moved from a first location in which the inspecting object is accessible to the scanning electron microscope to a second location in which the object is accessible to a focused ion beam miller and imager as disclosed in U.S. Pat. No. 6,670,610 assigned to the assignee of the present application. Ideally, during use of the system for defect detection and analysis, the electron beam 13 and the focused ion beam 14 shall be aimed to the same point on an object that is evaluated.

Note that the invention is not bound by the specific structure of the combined FIB/SEM system described with reference to FIGS. 1 and 2. Those versed in the art will readily appreciate that the invention is, likewise, applicable to any other combination of FIB with stand alone or integrated device for monitoring and/or inspection (e.g. Transmission Electron Microscope (TEM), Scanning Transmission electron microscope (STEM), etc.) as well as to imaging capability of the FIB system itself.

Figure 3:
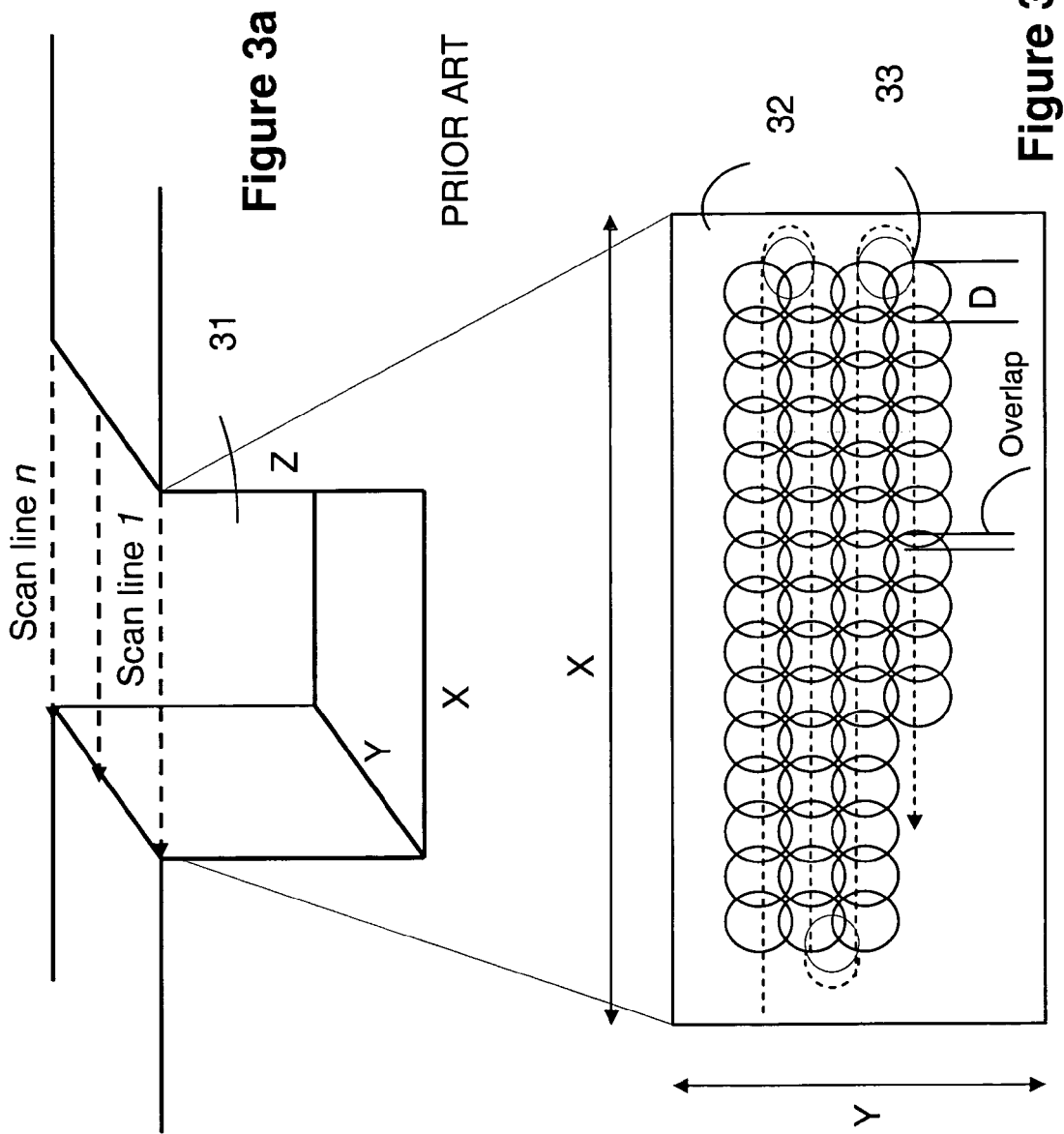
FIG. 3 illustrates a schematic view of typical regular cross-section and a milling frame.

Referring to FIG. 3*a*, there is illustrated a schematic view of regular cross-section 31 obtained within single milling frame comprising scanning of each milling line 33 within a milling area 32 with X*Y dimensions as schematically illustrated in FIG. 3*b*. The ion beam dwells at every pixel in the milling line and sputtering the material. The material removal rate (sputtering yield γ) is defined by the volume of material removed by each incident ion. The longer the beam milling a pixel, the more material is sputtered away at the object location corresponding to the pixel. Therefore, by controlling the milling time of the beam for each pixel, we can control over the milling depth. Assuming that each pixel has a unique dose and that the sputtering yield is constant with angle of incidence, the milling time T requiring achieve the depth h in material for a fixed spot with sputtering yield γ during a scanning with probe current Ip and beam spot diameter D is given by the following equation:

$$T = \frac{\frac{\pi}{4}D^2}{\gamma \cdot Ip} \cdot h \qquad (1)$$

Number of milling lines $N_{line}$ is defined as $$N_{line} = \frac{Y}{D} \cdot \frac{100\%}{100\% - Overlap\ \%}; \qquad (2)$$

and the time of scanning (milling) of one line $T_{line}$ is defined as $$T_{line} = \frac{T \cdot X}{D} \cdot \frac{100\%}{100\% - Overlap\ \%}. \qquad (3)$$

In the particular case of illustrated regular cross-section the depth h of each line is equal. In this case the total milling time is defined as $$T_{total} = \frac{X \times Y}{\gamma \cdot Ip} \cdot h. \qquad (4)$$

Typically, the time between one spot to the next spot in one line of milling (dwell time) is constant, and lines within one milling frame are scanning several times (hereinafter repetitions) before moving to the next milling line. The number of repetitions $N_r$ is defined as $$N_r = \frac{T_{total}}{T_{line} \times N_{line}} \qquad (5)$$

Figure 4:
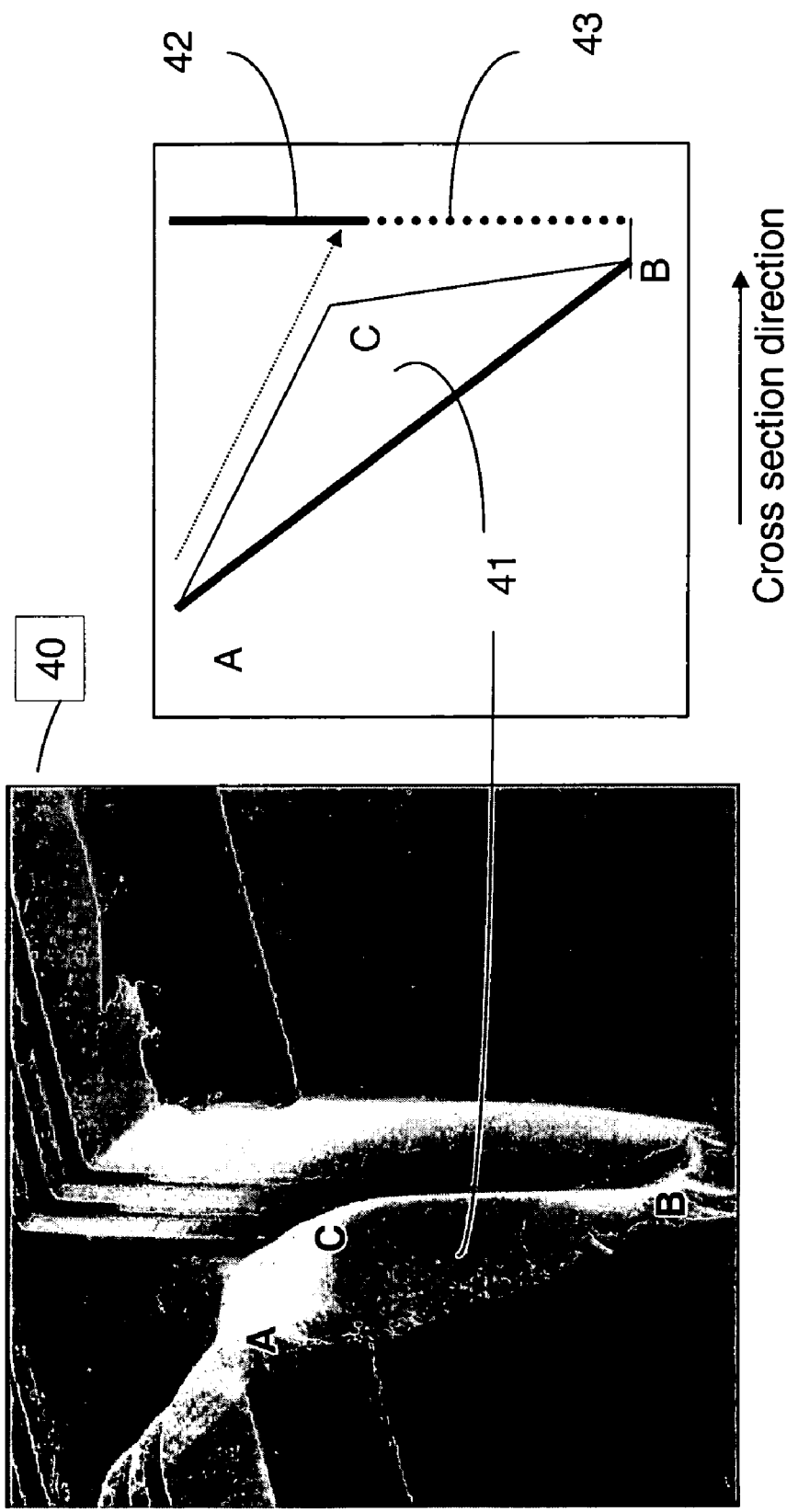
FIG. 4 illustrates experimental image of a cross section slope and its schematic side view.

In general case, the desired depth of different milling lines of the cross-section slope may be different (typically gradually increasing) as illustrated, for example, in FIG. 4. The number of scanning repetition for each line is defined by milling time required to achieve the depth predefined for the line (please see equation (3)).

Referring to FIG. 4, there is illustrated experimental image of a cross-section slope of a wafer 40 with re-deposition phenomena and its schematic side view (the similar re-deposition phenomena is happening for regular cross-section). The experimental image was obtained with following parameters:

Cross-section slope mode as known in the prior art; probe current Ip=500 pA; milling area X,Y,Z[um]=5×5×3; Line time $T_{line}$=33 μs; line number $N_{line}$=33; line repetition=229568; milling time $T_{total}$=500 sec; Dwell time=1 μsec; Overlap=50%.

The re-deposition phenomena may be caused by several reasons, e.g. positive charged surface after milling, dipole molecules or atoms caused by charge surface, open and free surface collecting milled molecules or atoms, etc. The re-deposition artifact ABC (41) is blocking the view of area 43 (dotted line) limiting the available (e.g. for inspection) image only by the area 42. These re-deposition phenomena may also cause voids during the subsequent process, e.g. when covering the cross-section area with isolated materials after analysis. The typical request for after-analysis process is to cover the cross-section hole with a flat top surface less than 500 nm higher from wafer surface and with no voids under the isolated surface. The re-deposition phenomena complicates this process, requiring first a filling of the cross-section trench with low probe current and small filed of view and only then a filling of the full cross-section area.

Figure 5:
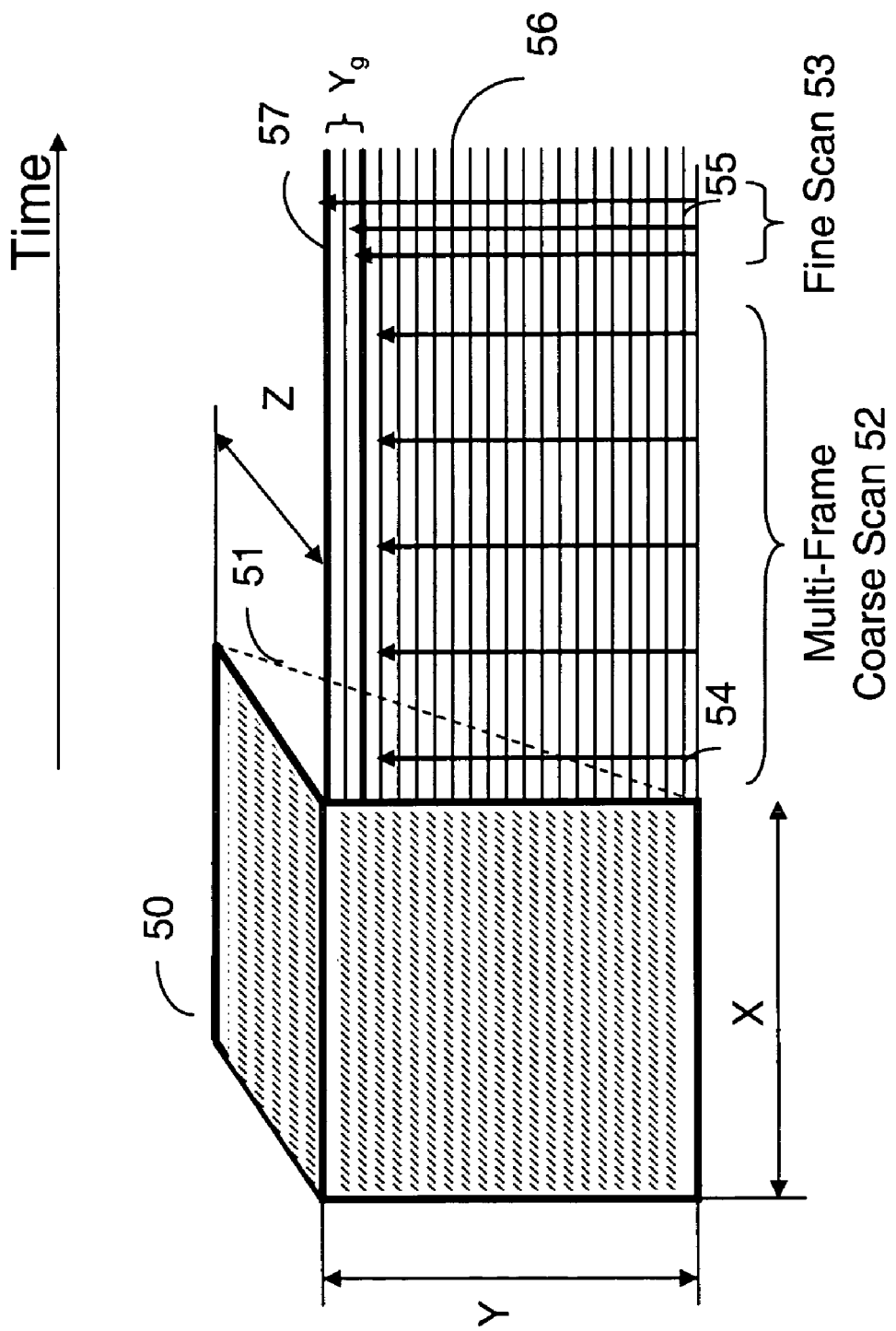
FIGS. 5-7 schematically illustrate the method of cross-section milling in accordance with certain embodiments of the present invention.
Figure 6:
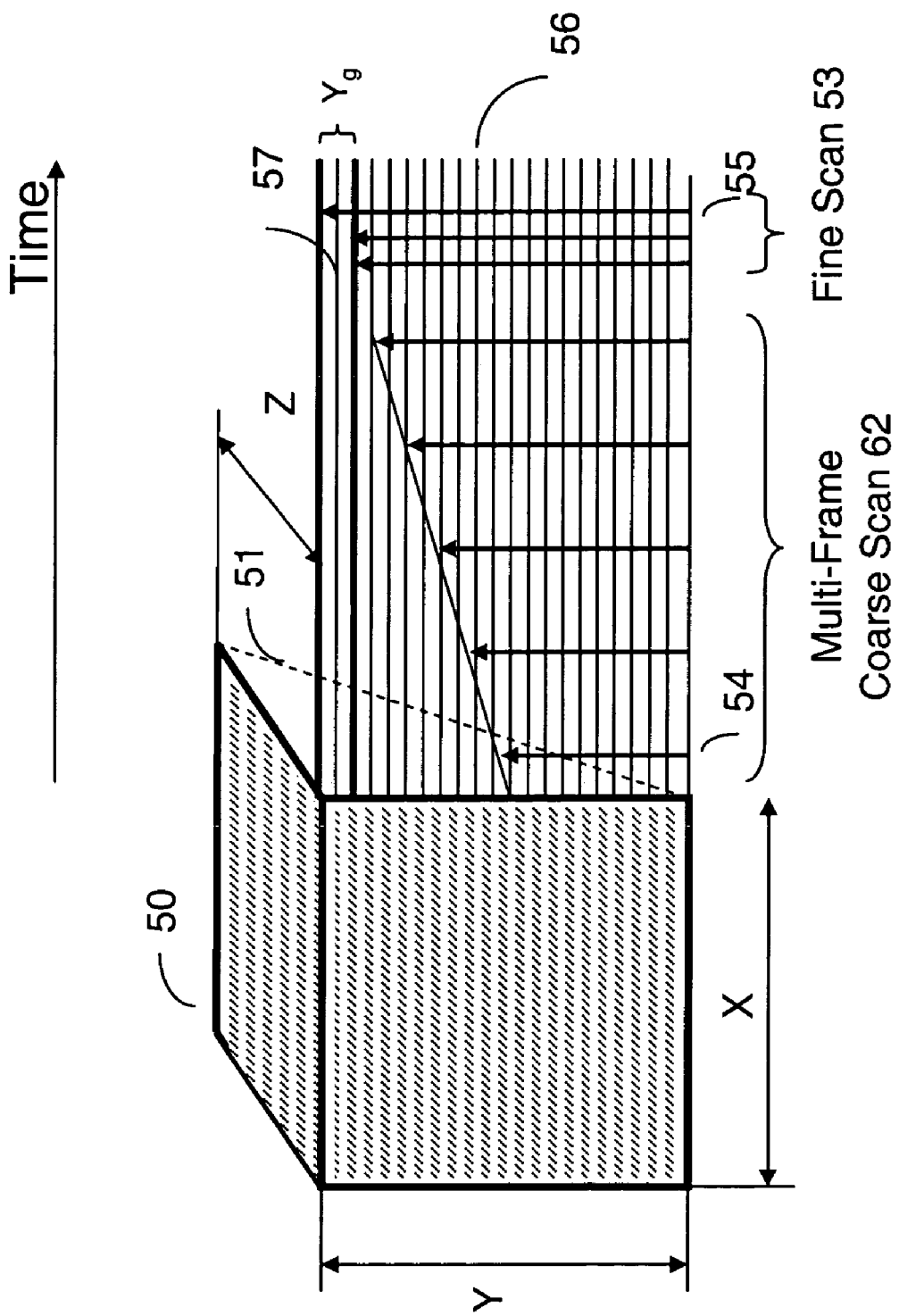
Figure 7:
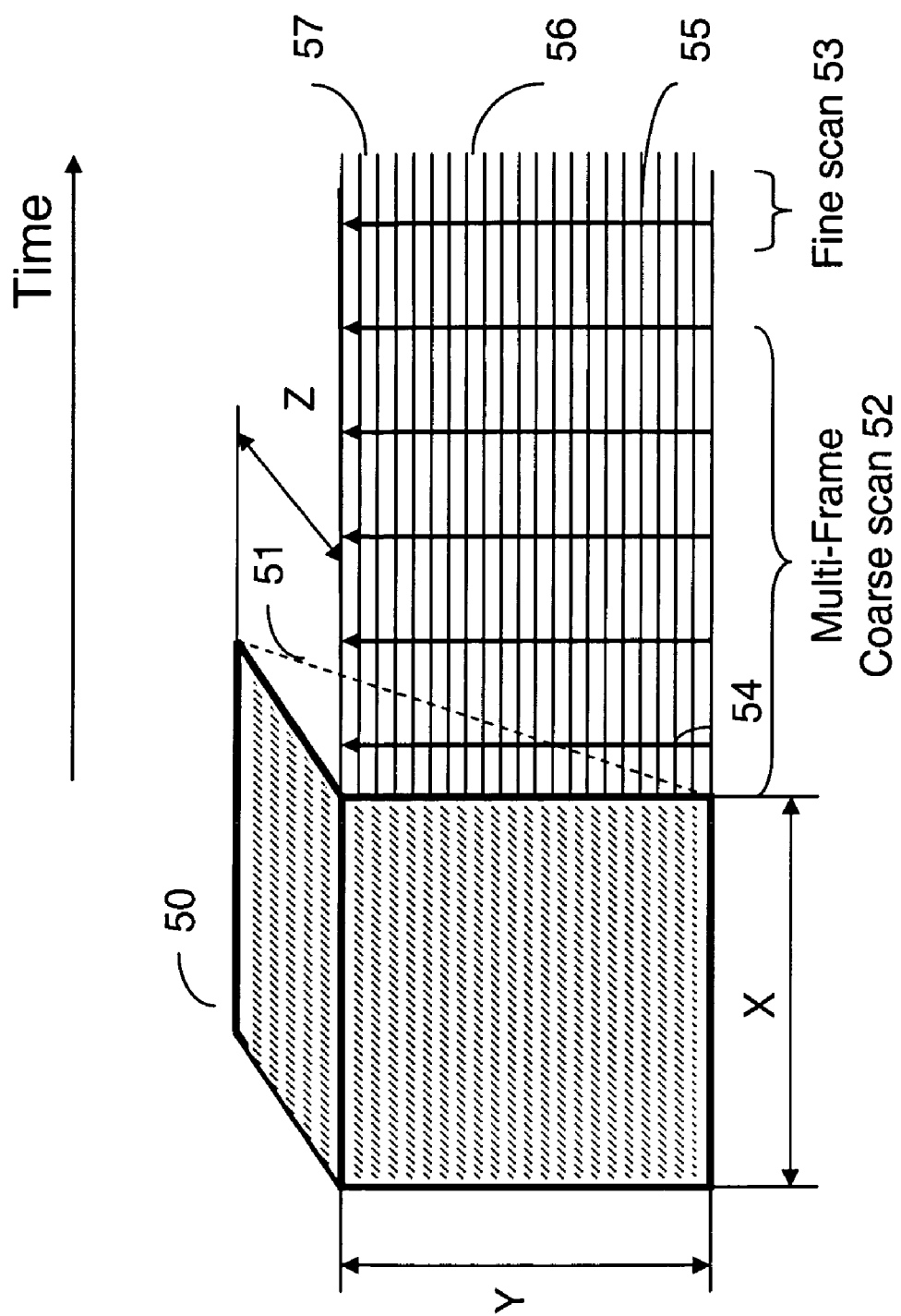

FIGS. 5-7 are schematically illustrate, by way of non-limiting example, the method of cross-section milling in accordance with certain embodiments of the present invention. As will be further illustrated by experimental results in FIGS. 9 and 10, the re-deposition depends upon how the milling is done. In accordance with certain embodiments of the present invention, the milling of a cross-section slope 51 in a wafer 50 by scanning the milling lines 56 comprises a step of a coarse scanning 52 and a step of fine scanning 53. The milling parameters of the coarse scanning differ from milling parameters of the fine scanning in at least one of the following:

the beam spot size within the coarse scanning is more than the beam size within the fine scanning;

a pixel overlapping within the coarse scanning is less than within the fine scanning;

coarse scanning is provided in a line-interlace mode as be further detailed in FIG. 8.

The beam spot size depends on FIB parameters and the probe current. The following Table 1 illustrates, by way of non-limiting example, experimental results of spot size measuring depending on the probe current, aperture size and condenser.

TABLE 1

| # | Ip [pA] | Aperture size [μm] | Condenser [v] | Spot size [nm] |
|---|---|---|---|---|
| 1 | 1 | 10 | 20500 | ~50 |
| 2 | 10 | 20 | 22222 | ~80 |
| 3 | 70 | 50 | 22222 | ~80 |
| 4 | 250 | 100 | 22222 | ~200 |
| 5 | 500 | 150 | 22222 | ~300 |
| 6 | 1000 | 200 | 22222 | ~500 |
| 7 | 5000 | 400 | 22600 | ~700 |
| 8 | 15000 | 400 | 23100 | ~1200 |

The step of coarse scanning comprises several milling frames 54; the step of fine scanning may comprise one (as illustrated in FIG. 7) or more (as illustrated in FIGS. 5 and 6) milling frames 55. The total dose to be radiated to each pixel of the cross-section and, accordingly, the number of sputtered atoms is defined by the sputtered yield and the desired cross-section slope profile (see, for example, equations (1)-(3)). However, the multi-frame scanning disclosed in the present invention, causes less re-deposition to occur than a single frame milling of the Prior Art (as will be further illustrated by experimental results in FIGS. 9 and 10). Some of the reasons are following: the multi-frame scanning facilitates to use some fraction of the primary beam for sputtering away the material re-deposited during previous milling frames; the multi-frame scanning facilitates time breaks in milling of each line thus reducing the surface charging; etc.

In the embodiments illustrated in FIG. 7 the coarse scan and the fine scan are milling the same area, the coarse scan is used for relatively fast coarse excavating and the fine scan for smoothing of the resulting rough milled surface. In the embodiments illustrated in FIGS. 5 and 6, the number of scanned lines 56 in the milling frames during the coarse scan is less than the total number (as defined by the equation (3)) of milling lines in the milling area on a number NA. The gap 57 may be predefined (for example, in accordance with a size of area of interest for further analysis), and $N_A$ may be defined in accordance with the size $Y_g$ of the gap 57 as $$N_\Delta = \frac{Y_g}{D} \cdot \frac{100\%}{100\% - Overlap\ \%}$$

Thus, in these cases, the coarse scan is excavating the non-important surface while the fine scan facilitates accurate milling of $N_A$ lines of the area of interest.

Those versed in the art will readily appreciate that the invention is, likewise, applicable to any other combination of milling lines during the coarse and the fine scan. After the milling is finished, the section slope may be further polished for improving the image of the analyzing surface.

According to certain embodiments of the present invention, the pixels overlapping may differ for different milling frames. The overlap reduction decreases the milling time, but leads to the rougher milling surface. In certain embodiments, the coarse scan may be provided, for example, with low overlap (e.g. 10%) and the fine scan with high overlap (e.g. 50% default overlap). In other embodiments of the present invention, the overlap may gradually grow with each next milling frame. Those versed in the art will readily appreciate that the invention is, likewise, applicable to any other variations of overlap between milling frames providing the optimization between milling time and the accuracy of milling.

In certain embodiments of the present invention as illustrated, e.g., in FIG. 5, the number of scanning lines in each of the multiple milling frames may be equal as well as a number of repetitions of the respective lines in different frames. In other embodiments of the present invention, the number of scanning lines and/or number of repetition for the respective line in different milling frames, may vary (e.g. gradually grow with each next milling frame as illustrated in FIG. 6). Those versed in the art will readily appreciate that the invention is, likewise, applicable to other variations of milling lines and their repetitions within multiple frames, providing that the total milling time of a pixel is sufficient to provide a predefined milling depth for that pixel.

In a general case, the total milling time $T^n$ of a pixel in a line number n during all milling frames scanning this line is connected with the predefined depth $h_n$ as following:

$$T^n = \sum_i T_i^n \cdot N_f^n = \frac{\frac{\pi}{4} \cdot h_n}{\gamma} \cdot \sum_i \frac{d_i^2}{Ip_i} \cdot N_f^n$$

where $T^n_i$ is a milling time of the pixel in the line n during the frame i, $N^n_f$—the number of milling frames scanning the line n, $D_i$—beam spot diameter during the frame i, $Ip_i$—probe current during the frame i.

Referring to FIG. 8, there is illustrated line-interlace mode of scanning in accordance with certain embodiments of the present invention. The proposed line-interlace mode facilitates re-deposition suppressing because of, for example, reducing of unwanted potential changes on the surface thus reducing the number of charged molecules and atoms to be attracted back to the wafer surface. Also the interlace mode facilitates reduction of total milling time.

In the line-interlace mode, the milling lines within a frame are divided in a number of groups $N_{group}$ ($N_{group}=3$ in the illustrated case) wherein the number of next line in the group $N_i$ is connected with a number of previous line in the group $N_{i-1}$ as $$N_i = N_{i-1} + int\left(\frac{N_{line}}{N_{group}}\right),$$

, where "int" stands for the integer part of the ratio.

The line-interlace milling starts with the scanning of lines among the first group (FIG. 8a), then scanning the lines of the next group (FIG. 8b), etc. until all the milling lines in the frame are scanned (FIG. 8c). Each line may be scanned with appropriate number of repetitions before moving to the next line. The next scanning group may start at the line next to the starting line of the previous group, at the middle line between two lines of the previous group, etc. Those versed in the art will readily appreciate that the invention is, likewise, applicable to any other algorithm of the line-interlace scanning.

Figure 9:
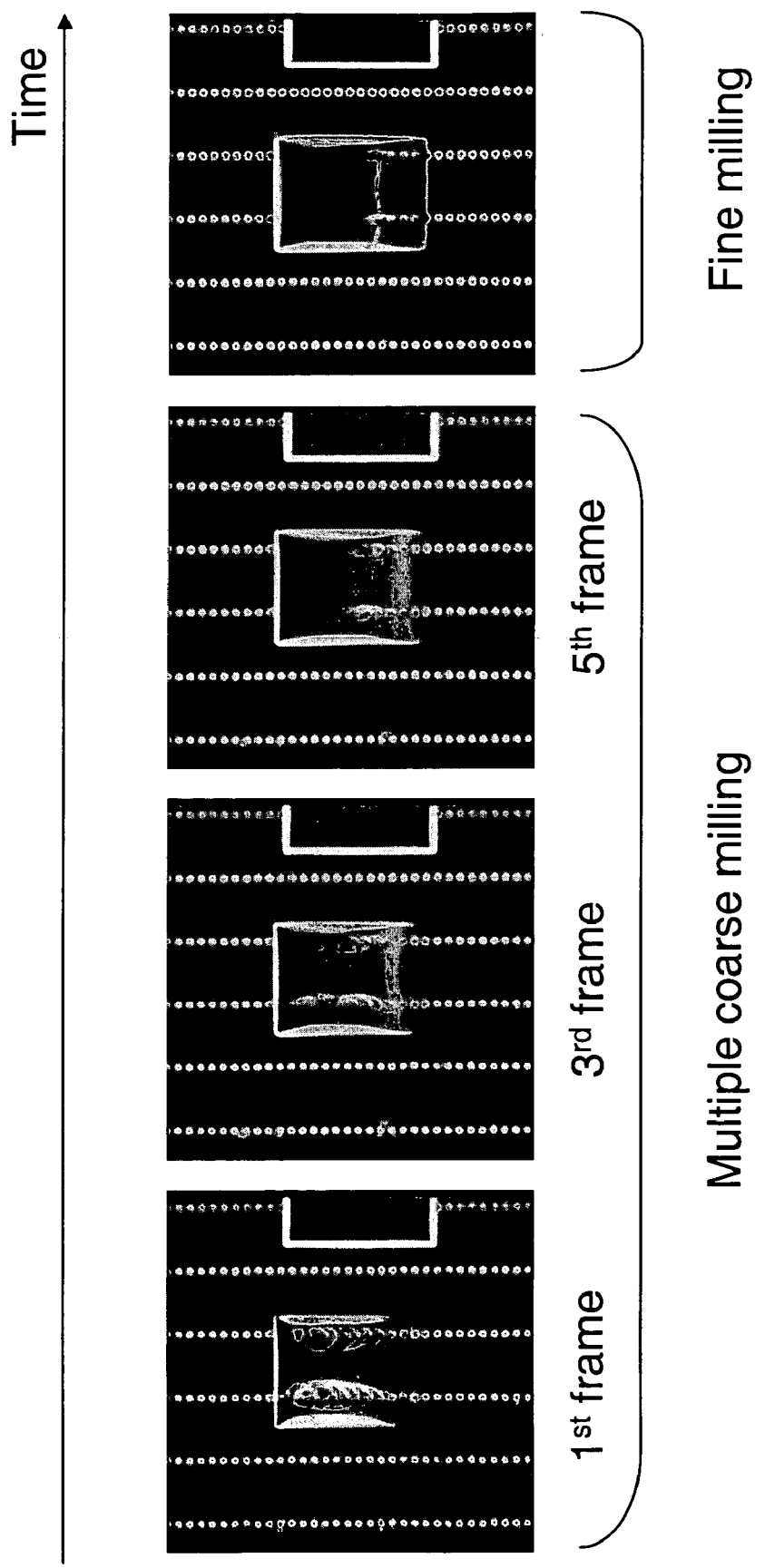
FIG. 9 illustrates experimental images received during cross-section milling in accordance with certain embodiments of the present invention

Referring to FIG. 9, there are illustrated experimental images (FOV=20 μm, current 500 pA, total time 1:37 min, milling area=6×8×0.5 μm, overlap 50%) received during 6-frame coarse milling and 1 frame fine milling.

Referring to FIG. 10 a) and b), there are illustrated, by way of non-limiting example, experimental images of cross-sections provided, accordingly, by regular and by multi-frame milling (3-frame coarse milling and 1 frame fine milling). With overall milling process less than two minutes (vs. 6.5 min. by the regular process), the multi-frame milling facilitates 0.9 μm deeper view of the wall slope.

The parameters of some experimental milling provided results similar to illustrated in FIGS. 9 and 10 are summarized in the following Table 2 by way of non-limiting example.

|  | Parameters of experimental milling in accordance with prior art | Parameters of experimental milling in accordance with certain embodiments of the present invention |
|---|---|---|
| Mode | Cross section slope | Cross section slope |
| Probe current [pA] | 500 | 500 |
| Spot size [nm] | 300 | 300 |
| Dwell time [μsec] | 1 | 1 |
| Overlap [%] | 50 | 50 |
| Number of frames | 1 | Coarse: interlace scanning up to 20 frames, default = 10; Fine: up to number of coarse frames, default = 3 |
| Gap | 1 (for polish) | Coarse: from 0 to 6 lines, default 3; Fine: from 0 to 6 lines, default 1. |

It is to be understood that the invention is not limited in its application to the details set forth in the description contained herein or illustrated in the drawings. The invention is capable of other embodiments and of being practiced and carried out in various ways. Hence, it is to be understood that the phraseology and terminology employed herein are for the purpose of description and should not be regarded as limiting. As such, those skilled in the art will appreciate that the conception upon which this disclosure is based, may readily be utilized as a basis for designing other structures, methods, and systems for carrying out the several purposes of the present invention.

It will also be understood that the invention further contemplates a machine-readable memory tangibly embodying a program of instructions executable by the machine for executing the method of the invention.

Those skilled in the art will readily appreciate that various modifications and changes can be applied to the embodiments of the invention as hereinbefore described without departing from its scope, defined in and by the appended claims.

The invention claimed is:

1. A method of cross-section milling of a wafer comprising: a coarse scanning of at least two milling frames and a fine scanning of at least one milling frame.

2. The method of claim 1 wherein a total milling period of a milling pixel is defined such as to provide a pre-defined milling depth.

3. The method of claim 1 wherein a number of scanning lines in a milling frame within the coarse scanning is larger than a number of scanning lines within a previous milling frame within the coarse scanning.

4. The method of claim 3 wherein a total milling period of a milling pixel within the coarse scanning is defined such as to provide a predefined for the coarse scanning milling depth.

5. The method of claim 1 wherein the coarse scanning comprises at least two frames with different number of scanning lines.

6. The method of claim 5 wherein the total milling period of a milling pixel within the coarse scanning is defined such as to provide a predefined for the coarse scanning milling depth.

7. The method of claim 1 further comprising scanning lines repeatedly within a milling frame.

8. The method of claim 7 wherein a number of scanning repetitions of a milling line in a milling frame within the coarse scanning is larger than a number of scanning repetitions of said line in a previous milling frame within the coarse scanning.

9. The method of claim 8 wherein the total milling period of a milling pixel within the coarse scanning is defined such as to provide a predefined for the coarse scanning milling depth.

10. The method of claim 7 wherein the coarse scanning comprises at least two milling frames with different number of scanning repetitions of corresponding milling lines.

11. The method of claim 10 wherein the total milling period of a milling pixel within the coarse scanning is defined such as to provide a predefined for the coarse scanning milling depth.

12. The method of claim 1 wherein at least one milling frame within the fine scanning comprises at least one line skipped during the coarse scanning.

13. The method of claim 12 wherein at least one of the skipped lines is the last line in the milling area.

14. The method of claim 1 wherein said scanning is providing with pixels' overlapping, the degree of said overlapping within the coarse scanning is less than said degree within the fine scanning.

15. The method of claim 1 wherein said scanning is providing with a beam having larger spot size within the coarse scanning than within the fine scanning.

16. The method of claim 1 wherein the coarse scanning comprises at least one frame provided in a line-interlace mode.

17. The method of claim 1 wherein the total milling time $T^n$ of a pixel in a milling line number n during all milling frames scanning this line is connected with the predefined for this line milling depth $h_n$ as following:

$$T^n = \sum_i T_i^n \cdot N_f^n = \frac{\frac{\pi}{4} \cdot h_n}{\gamma} \cdot \sum_i \frac{D_i^2}{Ip_i} \cdot N_f^n$$

where $T^n_i$ is a milling time of the pixel in the line n during the frame i, $N^n_f$ is the number of milling frames scanning the line n, $D_i$—beam spot diameter during the frame i, $Ip_i$—probe current during the frame i.

18. A method for cross-section milling of a wafer comprising scanning of at least two milling frames with milling parameters configured as at least one of the following:

a beam spot size during one milling frame is larger than a beam spot size during a different milling frame among said at least two milling frames;

a pixels' overlapping degree during one milling frame is less than a pixels' overlapping degree during a different milling frame among said at least two milling frames;

the scanning in one milling frame among said at least two milling frames is provided in a line-interlace mode.

19. A milling device adapted to cross-section milling of a wafer, said milling comprising a coarse scanning of at least two milling frames and a fine scanning of at least one milling frame.

20. A computer program product comprising a computer useable medium having computer readable program code embodied therein of cross-section milling of a wafer, the computer program product facilitating a coarse scanning of at least two milling frames and fine scanning of at least one milling frame.

* * * * *